(12) United States Patent
Hesselink et al.

(10) Patent No.: US 10,859,517 B2
(45) Date of Patent: Dec. 8, 2020

(54) SINGLE X-RAY GRATING X-RAY DIFFERENTIAL PHASE CONTRAST IMAGING SYSTEM

(71) Applicants: The Board of Trustees of the Leland Stanford Junior University, Palo Alto, CA (US); University of Arizona, Tucson, AZ (US)

(72) Inventors: Lambertus Hesselink, Atherton, CA (US); Max Yuen, San Francisco, CA (US); Yao-Te Cheng, New Taipei (TW); Yuzuru Takashima, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 413 days.

(21) Appl. No.: 15/640,092

(22) Filed: Jun. 30, 2017

(65) Prior Publication Data
US 2017/0307549 A1 Oct. 26, 2017

Related U.S. Application Data

(63) Continuation-in-part of application No. 15/490,194, filed on Apr. 18, 2017, now abandoned.
(Continued)

(51) Int. Cl.
*H01J 35/06* (2006.01)
*G01N 23/20* (2018.01)
(Continued)

(52) U.S. Cl.
CPC ..... *G01N 23/20075* (2013.01); *A61B 6/4241* (2013.01); *A61B 6/483* (2013.01);
(Continued)

(58) Field of Classification Search
CPC .......... A61N 2005/1019; A61N 5/1028; A61B 6/4429; A61B 6/44; A61B 6/40; G01N 23/083; G21G 4/00
See application file for complete search history.

(56) References Cited

U.S. PATENT DOCUMENTS 6,011,874 A * 1/2000 Gluckstad .............. G02B 27/52
359/559
9,520,260 B2 * 12/2016 Hesselink ............. H01J 35/065
(Continued)

OTHER PUBLICATIONS

Ge et al., "Grating based x-ray differential phase contrast imaging without mechanical phase stepping", 2014, Optics Express v22n12, pp. 14246-14252.
(Continued)

*Primary Examiner* — David P Porta
*Assistant Examiner* — Mamadou Faye
(74) *Attorney, Agent, or Firm* — Beyer Law Group LLP (57) ABSTRACT

Single X-ray grating differential phase contrast (DPC) X-ray imaging is provided by replacing the conventional X-ray source with a photo-emitter X-ray source array (PeXSA), and by replacing the conventional X-ray detector with a photonic-channeled X-ray detector array (PcXDA). These substitutions allow for the elimination of the G0 and G2 amplitude X-ray gratings used in conventional DPC X-ray imaging. Equivalent spatial patterns are formed optically in the PeXSA and the PcXDA. The result is DPC imaging that only has a single X-ray grating (i.e., the G1 X-ray phase grating).

17 Claims, 12 Drawing Sheets

Related U.S. Application Data (60) Provisional application No. 62/324,326, filed on Apr. 18, 2016.

(51) Int. Cl.
*G01T 1/20* (2006.01)
*A61B 6/00* (2006.01)
*G01N 23/041* (2018.01)

(52) U.S. Cl.
CPC ......... *G01N 23/041* (2018.02); *G01T 1/2002* (2013.01); *G01T 1/2018* (2013.01); *A61B 6/484* (2013.01)

(56) References Cited

U.S. PATENT DOCUMENTS

| | | | |
|---|---|---|---|
| 2006/0237653 A1* | 10/2006 | Popescu | G01T 1/201 250/367 |
| 2009/0238449 A1* | 9/2009 | Zhang | G01B 11/2536 382/165 |
| 2009/0316857 A1 | 12/2009 | David et al. | |
| 2010/0027739 A1* | 2/2010 | Lanza | G02B 27/52 378/37 |
| 2012/0057676 A1 | 3/2012 | Koehler et al. | |
| 2012/0263271 A1* | 10/2012 | Aleshin | G21C 3/623 376/426 |
| 2014/0265828 A1 | 9/2014 | Maldonado et al. | |
| 2015/0036805 A1* | 2/2015 | Fu | G01N 23/201 378/145 |
| 2015/0182178 A1* | 7/2015 | Baturin | G01N 23/20075 378/36 |
| 2017/0038481 A1 | 2/2017 | Cheng et al. | |
| 2018/0344268 A1* | 12/2018 | Koehler | A61B 6/4035 |

OTHER PUBLICATIONS

Pfeiffer et al., "Phase retrieval and differential phase-contrast imaging with low-brilliance X-ray sources", 2006, Nature Physics v2, pp. 258-261.

\* cited by examiner

SINGLE X-RAY GRATING X-RAY DIFFERENTIAL PHASE CONTRAST IMAGING SYSTEM

CROSS REFERENCE TO RELATED APPLICATIONS

This application is a continuation in part of U.S. Ser. No. 15/490,194, filed on Apr. 18, 2017 and hereby incorporated by reference in its entirety.

Application Ser. No. 15/490,194 claims the benefit of U.S. provisional patent application 62/324,326, filed on Apr. 18, 2016, and hereby incorporated by reference in its entirety.

GOVERNMENT SPONSORSHIP

This invention was made with Government support under contract HSHQDC-12-C-00002 awarded by the Department of Homeland Security, Science and Technology. The Government has certain rights in the invention.

FIELD OF THE INVENTION

This invention relates to differential phase contrast X-ray imaging.

BACKGROUND

Differential phase contrast (DPC) X-ray imaging is used in a wide variety of applications, because it can provide superior performance compared to conventional imaging. However, conventional approaches for performing DPC X-ray imaging suffer from disadvantages mainly caused by the need to have two X-ray amplitude gratings in the system. Accordingly, it would be an advance in the art to provide DPC imaging that does not suffer from these disadvantages.

SUMMARY

We provide single X-ray grating DPC X-ray imaging by replacing the conventional X-ray source with a photo-emitter X-ray source array (PeXSA) as described in greater detail below, and by replacing the conventional X-ray detector with a photonic-channeled X-ray detector array (PcXDA) as described in greater detail below. These substitutions allow for the elimination of the G0 and G2 amplitude X-ray gratings used in conventional DPC X-ray imaging. Equivalent spatial patterns are formed optically in the PeXSA and the PcXDA. The result is DPC imaging that only has a single X-ray grating (i.e., the G1 X-ray phase grating).

An exemplary embodiment is apparatus for performing X-ray differential phase contrast imaging, where the apparatus includes: an X-ray source having a photo-emitter X-ray source array; an X-ray detector having a photonic-channeled X-ray detector array; and an X-ray phase grating disposed between the X-ray source and the X-ray detector. Here the apparatus includes no X-ray grating other than the X-ray phase grating, in marked contrast to conventional DPC approaches.

The photo-emitter X-ray source array can include: a light source; a spatial light modulator configured to receive light from the light source and to provide an optical spatially patterned beam; a photocathode configured to receive the optical spatially patterned beam and to provide patterned electron emission having an electron pattern according to the optical spatially patterned beam; electron optics configured to receive the patterned electron emission and to provide an electron image of accelerated electrons according to the electron pattern; and an X-ray target disposed to receive the electron image of accelerated electrons and to provide patterned X-ray emission according to the electron image.

The photonic-channeled X-ray detector array can include: a scintillator configured to receive X-rays and to provide corresponding optical radiation; an optical subsystem configured to receive the optical radiation and to provide an optical image; an optical detector array configured to receive the optical image and to provide a detector signal corresponding to the optical image. The PcXDA can further include further an optical grating mask configured to mask the optical image according to a grating mask pattern. Possibilities for this mask include a fixed or scannable metal grating, and a liquid crystal device array.

The optical subsystem of the PcXDA can include: a first telecentric lens array; a second telecentric lens array; and a phase coded aperture disposed between the first telecentric lens array and the second telecentric lens array. Here the optical subsystem is configured as a 4f imaging system where a Fourier transform of the optical radiation is formed at the location of the phase coded aperture, and where a Fourier transform of optical radiation transmitted through the phase coded aperture is formed as the optical image at the location of the optical grating mask.

Methods of performing X-ray differential phase contrast imaging are also provided, the most general such method including providing apparatus of as described above and analyzing X-ray fringe patterns.

The analyzing the X-ray fringe patterns can include scanning a detected X-ray fringe pattern at the photonic-channeled X-ray detector array by scanning a corresponding optical fringe pattern within the photo-emitter X-ray source array.

The analyzing the X-ray fringe patterns can include scanning a detected X-ray fringe pattern at the photonic-channeled X-ray detector array by altering a transmission pattern of an optical grating mask within the photonic-channeled X-ray detector array. The optical grating mask can include an array of liquid crystal optical transmission devices.

The analyzing X-ray fringe patterns can include analyzing a detected X-ray fringe pattern at the photonic-channeled X-ray detector array with an optical detector array within the photonic-channeled X-ray detector array, wherein the optical detector array has a pixel size of no more than 0.5 times a pitch of a detected X-ray fringe pattern.

The analyzing X-ray fringe patterns can include analyzing a detected X-ray fringe pattern at the photonic-channeled X-ray detector array using an optical grating mask within the photonic-channeled X-ray detector array that includes two or more distinct grating mask patterns to provide single-shot analysis of multiple phase patterns at once.

Significant advantages are provided:

1) The two high aspect ratio amplitude gratings (G0, G2), which are relatively difficult and expensive for fabrication, are no longer needed. Instead, PeXSA doesn't need a fixed pattern fabrication and the fabrication of a thin chromium mask in PcXDA as used in some embodiments only needs regular simple photolithography with metal lift-off.

2) PeXSA X-ray source creates a patterned partially spatially coherent X-ray source on a planar X-ray target. The aspect ratio of the patterned X-ray source is decided by (electron penetration depth in the X-ray target or, roughly, the thickness of the transmission target)/[(source grating pitch)×(duty cycle of bright source fringe)]. The value is normally less than unity, compared to the aspect ratio of a regular X-ray source grating (G0) in FIG. 1, which is normally larger than 5:1 or a lot more for high X-ray energies. Using PeXSA X-ray source may largely enhance the FOV (field of view) of the X-ray DPC imaging system provided that the FOV is not limited by the analyzer amplitude grating G2.

3) PcXDA X-ray detector in some embodiments uses a chromium mask pattern that is 100-150 nm thick. The chrome mask aspect ratio is decided by (100-150 nm)/[(analyzer grating pitch)×(duty cycle of chrome opening width)]. The value is normally less than 0.1, which significantly enhance the FOV of the X-ray DPC imaging system provided that the FOV is not limited by the source amplitude grating. By replacing the source grating G0 and the analyzer grating G2 in FIG. 1 with PeXSA X-ray source and PcXDA detector, the FOV of the X-ray DPC imaging system can be significantly improved for any practical applications.

4) PeXSA X-ray source creates X-ray source of nearly 100% amplitude modulation depth according to the patterned electron beam bombarding the X-ray target, which may enhance the degree of partially spatial coherence of the X-rays in the imaging system and enhance the intensity contrast of the X-ray interference pattern. The chromium mask in front of the photodetector panel of PcXDA X-ray detector performs nearly 100% amplitude modulation depth because only 100-150 nm thick chromium can efficiently block nearly all of the fluorescent light in the visible wavelength range, which may enhance the visibility of the X-ray DPC image detected by the PcXDA X-ray detector. The enhancement of the X-ray DPC image visibility from both effect reduces X-ray image acquiring time.

5) Using the single-shot grating profile, the time to acquire an X-ray DPC image may be made faster by N times, provided N is the number of steps used in the regular phase stepping technique.

DETAILED DESCRIPTION

Figure 1:
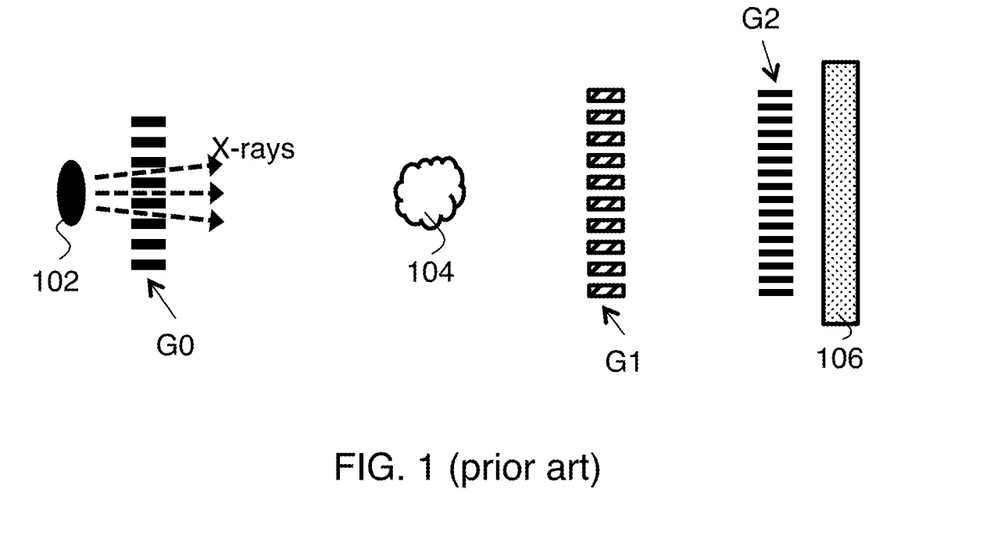
FIG. 1 shows conventional differential phase contrast X-ray imaging.

Conventional absorption-based X-ray imaging has been a valuable tool for aviation security inspection, medical imaging, and a variety of non-destructive imaging applications over decades. X-ray differential phase contrast (DPC) imaging technology has introduced two more dimensions of material properties—phase and small angle scattering (also called dark-field imaging), described below in connection with FIGS. 2A-B. This provides significant potentials in aviation security, medical imaging, and other non-destructive inspection imaging applications. The current standard X-ray DPC imaging system using a non-synchrotron radiation, incoherent X-ray source is a three grating based system as shown in FIG. 1.

Here an X-ray source 102 provides X-rays to a source amplitude grating G0 that is used to create partially spatially coherent X-rays emitting towards the phase grating G1 through object 104. X-rays transmitted through the phase grating G1 are diffracted and form an interference pattern at one of the Talbot self-imaging locations, where the analyzer amplitude grating G2 is located. Usually, the pixel dimension of an X-ray detector panel 106 is too large to resolve these X-ray interference patterns. A phase stepping technique is usually employed by moving the analyzer grating G2 in a few steps of a period (pitch) of the periodic X-ray interference pattern to resolve the X-ray interference pattern's intensity fluctuation in the lateral space dimension.

Figure 2A:
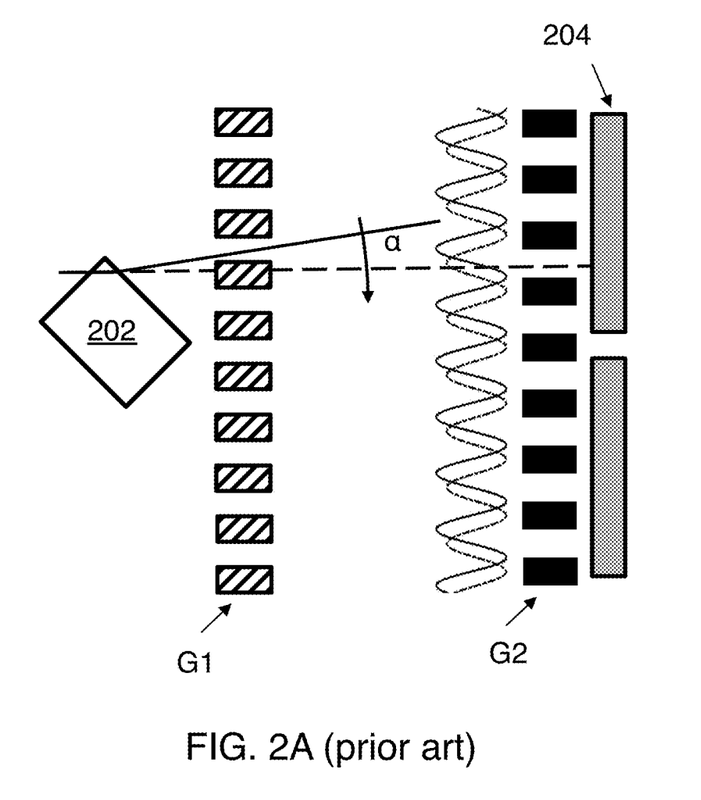
FIGS. 2A-B show operation of the system of FIG. 1.
Figure 2B:
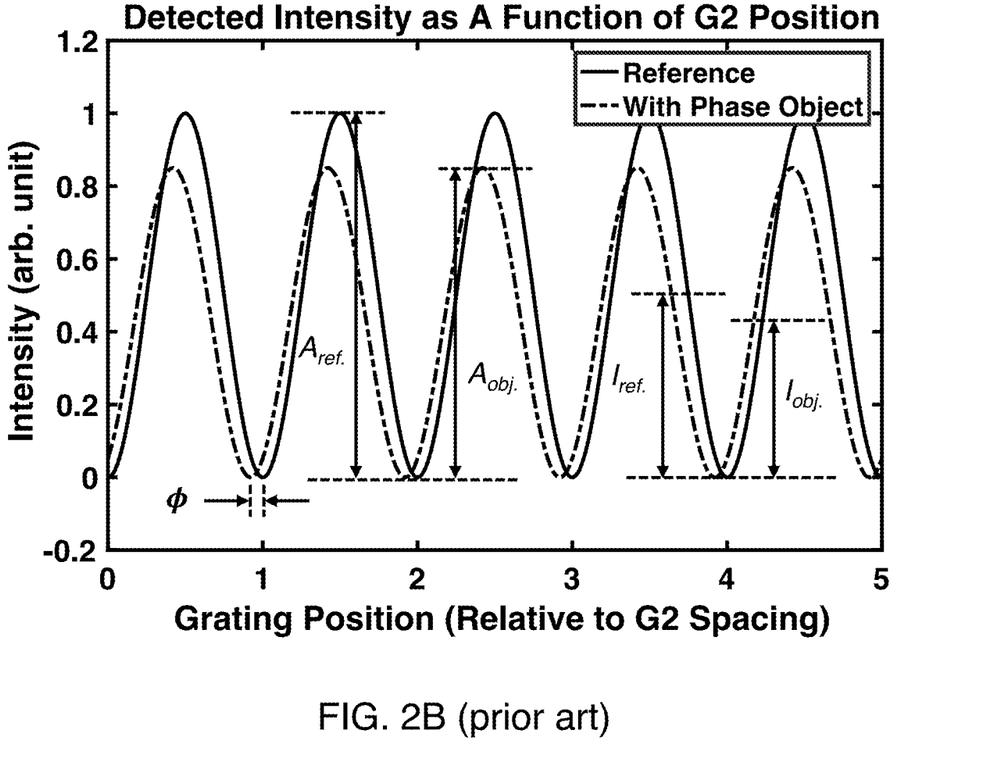

This operation is shown more explicitly on FIGS. 2A-B. Here 202 is the object being imaged and the angular deflection α is given by $$\alpha = \frac{\lambda}{2\pi} \frac{\partial \phi}{\partial x},$$

where $\lambda$ is the wavelength and $\phi$ is phase. The result of this angular deflection is a shift in fringe patterns as shown. More specifically, with reference to FIG. 2B, $\phi = \phi_{obj} - \phi_{ref}$ is the differential phase contrast signal, $V = (A_{obj}/I_{obj})/(A_{ref}/I_{ref})$ is the dark field signal and $\alpha_{abs} = I_{obj}/I_{ref}$ is the standard absorption signal.

Figure 3:
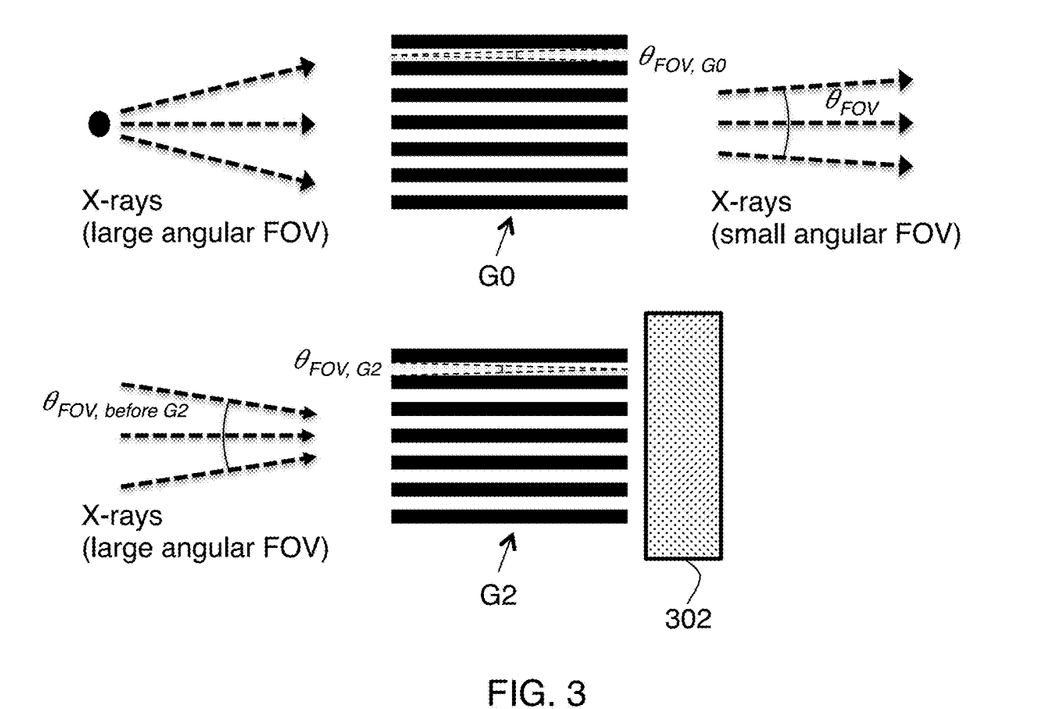
FIG. 3 shows how X-ray amplitude gratings G0 and G2 can undesirably reduce field of view.

Several aspects of the three grating X-ray DPC image system limit the applications of the X-ray DPC imaging technology in the real world. Among them, the limited imaging field of view (FOV), low fringe visibility, and long imaging times are major concerns. First, the imaging FOV is significantly limited by the two amplitude gratings, G0 and G2. The source amplitude grating G0 needs high amplitude modulation depth to get high degree of partially spatial coherence of X-rays. The analyzer amplitude grating G2 needs high amplitude modulation depth to get high analyzing image contrast at the X-ray detector. X-ray amplitude gratings are usually made of gold as gold has high attenuation coefficients of X-rays. However, despite the X-ray energies around the gold K-shell edge, higher X-ray energies need thicker gold to stop X-rays from penetrating through. Amplitude gratings of thicker gold form amplitude gratings of high aspect ratio, which significantly limits the X-rays coming from the source with a large angle. For a conventional 28 keV X-ray DPC system, the X-ray image at the object space can be limited to a few centimeters. FIG. 3 schematically shows the limited field of view caused by grating G0 (top half of figure) and by grating G2 (bottom half of figure). Here 302 is an X-ray detector.

Second, using an incoherent X-ray source, the X-ray DPC image visibility is usually 10-15%, which results in a relatively slow imaging time to get high quality X-ray DPC images. The image visibility can be improved by increasing the amplitude modulation depths of the two amplitude gratings; however, it limits the image FOV more, as mentioned in the previous paragraph, and also increases the difficulties of the grating manufacturing. In addition, the phase stepping of the analyzer grating G2 requires precise motion of moving the grating. This further reduces the overall imaging speed and stability.

In this work we replace the conventional X-ray source, X-ray detector and two amplitude gratings (G0 and G2) with a photo-emitter X-ray source array (PeXSA) as the partially spatially coherent X-ray source and a photonic-channeled X-ray detector array (PcXDA) as the analyzing X-ray detector. Two schematic systems are shown on FIGS. 4A-B. Here 410 is the PeXSA source and 420 is the PcXDA detector. As shown on FIGS. 4A-B, the object 104 can be either before or after phase grating G1 as one goes from source 410 to detector 420.

The PeXSA source 410 is described in detail in U.S. Pat. No. 9,520,260, hereby incorporated by reference in its entirety. FIG. 4C shows an exemplary PeXSA source 410. In this example, light from an optical source 411 (e.g., a laser) is patterned by a spatial light modulator (SLM) 412 and the resulting laser light pattern is imaged via optics 418 onto a photocathode 413 in the PeXSA. This laser light pattern can have the same pattern as the source grating G0 shown in FIG. 1. Photoelectrons 417 having this source grating pattern are excited at the opposite side of the photocathode 413. Then, the photoelectrons are accelerated by electron optics 414 through vacuum chamber 415 and imaged onto the X-ray tungsten target 416 when the photocathode is biased at a negative voltage compared to the voltage applied on the X-ray tungsten target 416. Electron optics 414 can include a solenoid lens to generate quasi-uniform axial magnetic field to obtain the same electron image pattern on the X-ray tungsten target 416 compared to the photoelectron pattern generated on the photocathode 413. Thus, an X-ray source of the same pattern as the electron image pattern on the X-ray tungsten target 416 is generated at the X-ray tungsten target 416. The X-ray source pattern may be slightly blurred compared to the electron image pattern on the X-ray tungsten target because of electron penetration and scattering in the X-ray tungsten target. The X-ray spectrum generated is dependent on the landing energy of the electron beam on the X-ray tungsten target. In one of the X-ray tungsten targets, we use a thin tungsten film (several micrometer thick, say 0.5 μm-15 μm, but can be thicker for higher electron beam landing energy) on a diamond substrate (100 μm to a few millimeters or thicker). Using a diamond substrate is preferred for dissipation of heat generated during electron beam bombardment of the X-ray tungsten target. The partially spatially coherent X-rays are then emitted from the patterned X-ray source in all directions. This operation of the PeXSA source is schematically shown on FIG. 4C.

Figure 4A:
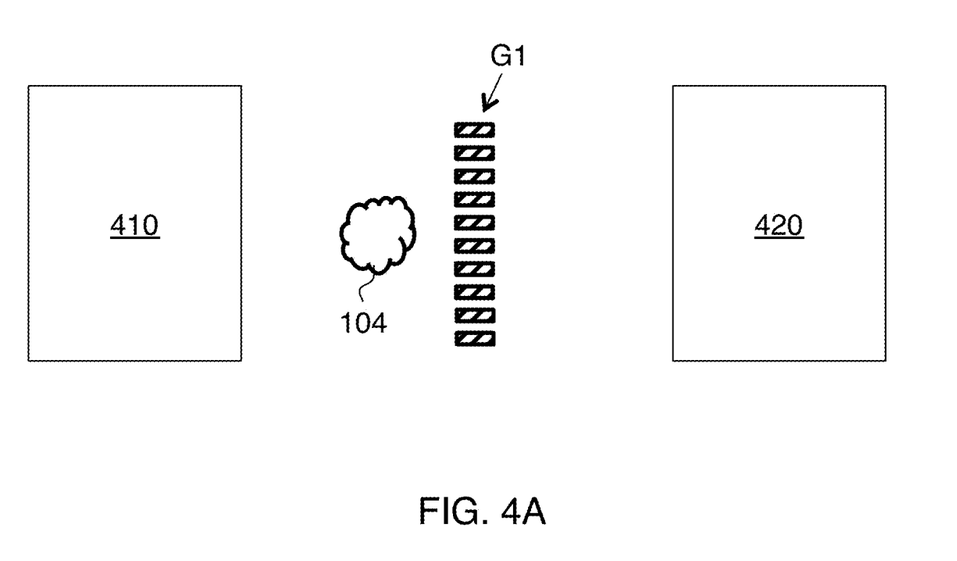
FIGS. 4A-B show overall block diagrams of two exemplary embodiments of the invention.
Figure 4B:
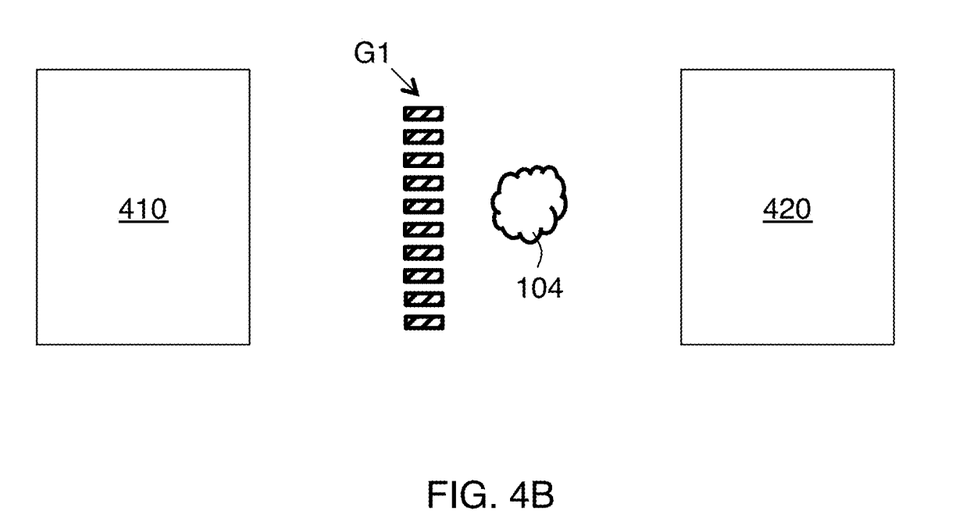
Figure 4C:
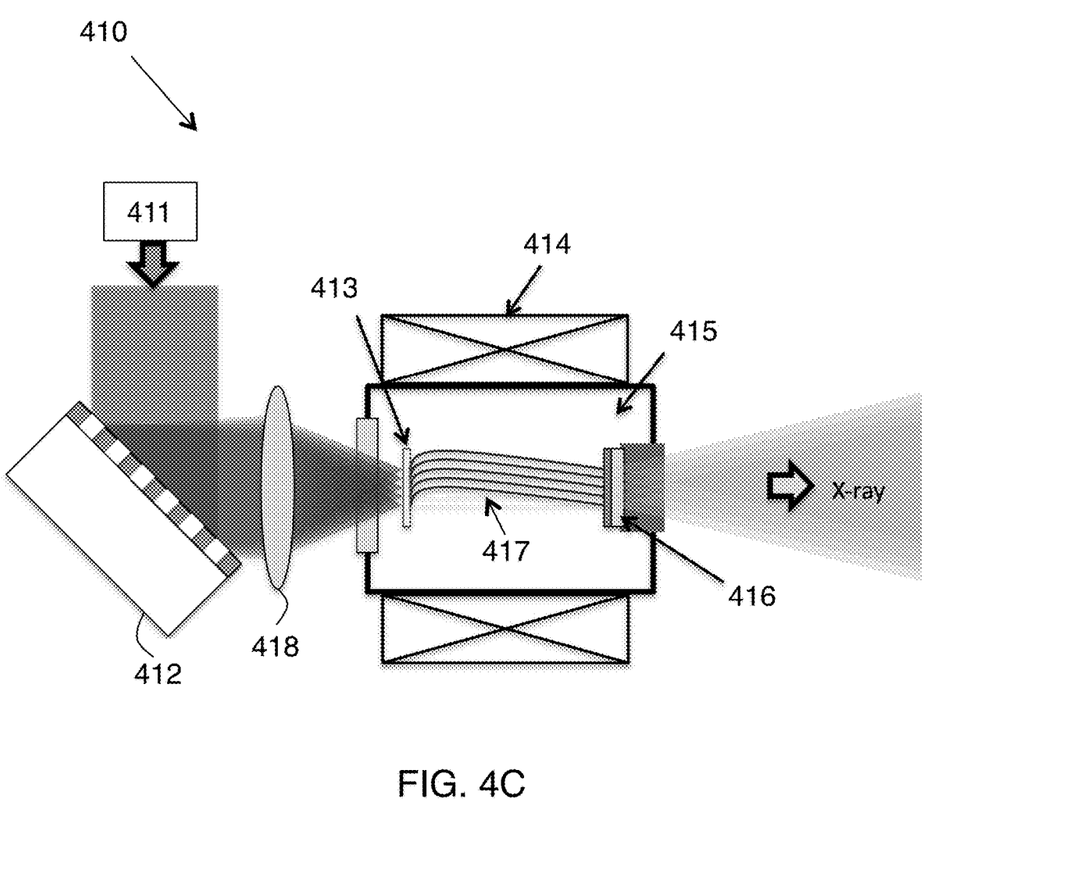
FIG. 4C shows an exemplary photo-emitter X-ray source array.
Figure 4D:
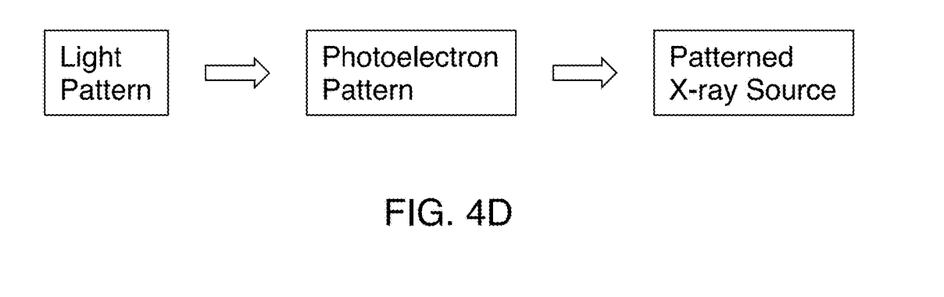
FIG. 4D schematically shows operation of a photo-emitter X-ray source array.

When PeXSA source 410 is operating in the configurations of FIG. 4A or 4B, we can direct the opposite surface of the X-ray tungsten target 416 towards an object 104 that we want to image with the X-ray DPC imaging system and a phase grating G1. The partially spatially coherent X-rays are then diffracted by the phase grating G1 with a phase of the wave front modified by the object. The X-ray interference pattern of such wave front modified diffracted X-rays is formed at one of the Talbot self-image locations. We locate the scintillator of the PcXDA X-ray detector 420 at one of the Talbot self-image locations in order to obtain X-ray images from high contrast X-ray interference pattern. In one of the operation modes of our DPC image system, we locate the scintillator of the PcXDA X-ray detector at the first order of Talbot self-image location.

Figure 4E:
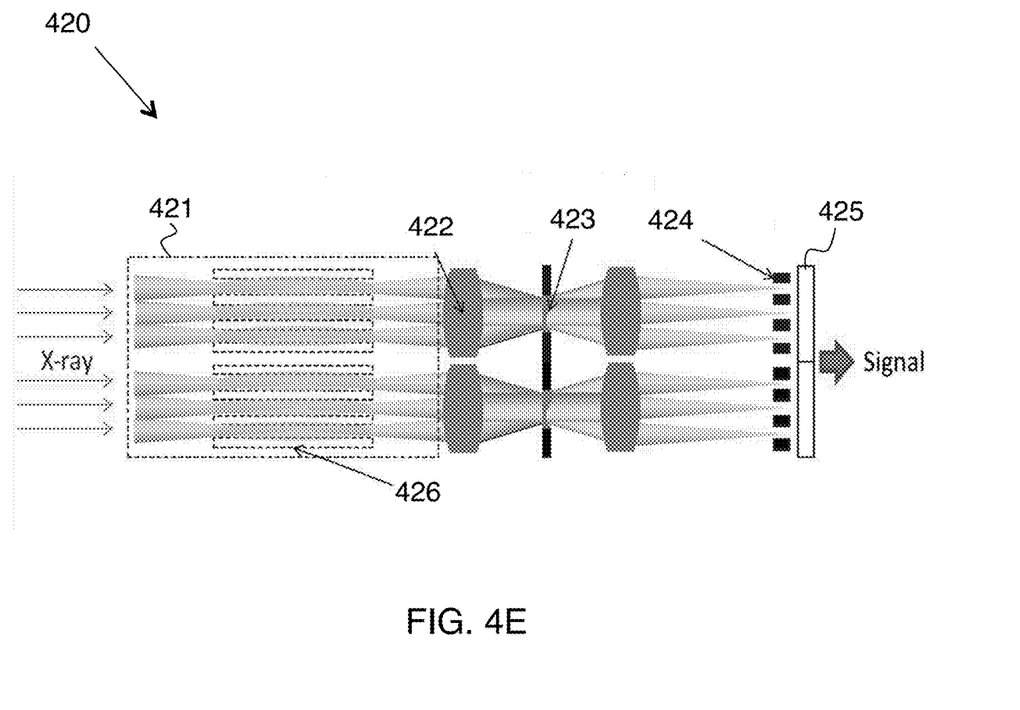
FIG. 4E shows an exemplary photonic-channeled X-ray detector array.
Figure 4F:
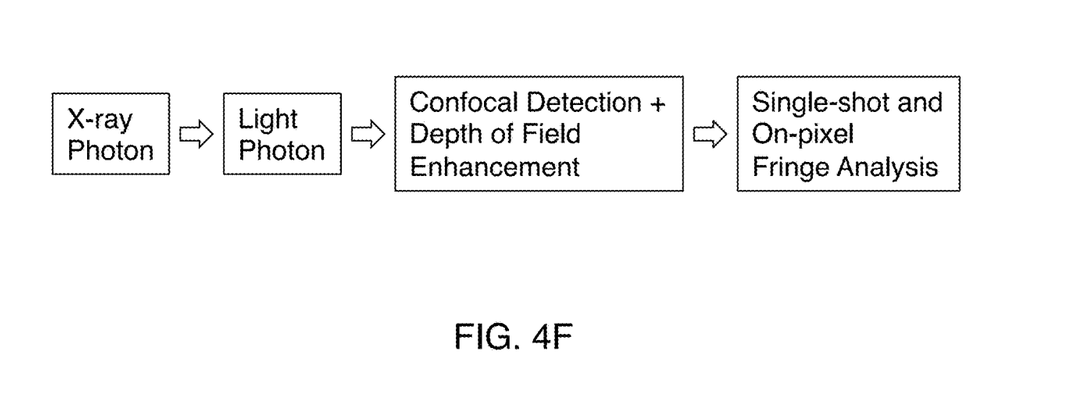
FIG. 4F schematically shows operation of a photonic-channeled X-ray detector array.

The PcXDA detector is described in detail in U.S. 2017/0038481, hereby incorporated by reference in its entirety. FIG. 4E shows an exemplary PcXDA detector 420. As shown in FIG. 4E, the X-ray interference pattern formed in the scintillator 421 of PcXDA 420 has a high aspect-ratio distribution (e.g., 2-20 μm in the lateral dimension and 100-500 μm in the longitudinal dimension). This distribution can be regarded as a virtual buried grating 426. The X-rays are transferred into fluorescent light pattern in the scintillator. We use a confocal detection configuration with micro-lens or micro-optics array 422 combined with a phase coded aperture 423 in PcXDA to transfer the X-ray interference pattern into fluorescent light pattern of the same shape at the photodetector array 425 of the PcXDA. Since the fluorescent light pattern is usually in the visible light wavelength range, the amplitude modulation of the optical grating 424 can be simply done by a very thin layer of metal (ex: ~5 times the skin depth of a metal, say 100-150 nm thick of chromium). In one of the methods to analyze the transformed optical pattern of the X-ray interference pattern, a thin film chromium grating of the same grating pitch as the analyzer amplitude grating G2 shown in FIG. 1 is made immediately in front of the photodetector array. Since the fluorescent light is in the visible light wavelength range, the amplitude modulation provided by optical grating 424 can also be performed using a panel of liquid crystal arrays similar to the liquid crystal display (LCD). The liquid crystal pixels can be turned on or off to allow or block the fluorescent light pattern to transmit or from being transmitted to the photodetector, which may be dynamically changed. A liquid crystal array panel may also be made immediately in front of the photodetector array. This operation of the PcXDA detector is schematically shown on FIG. 4F.

Figure 5:
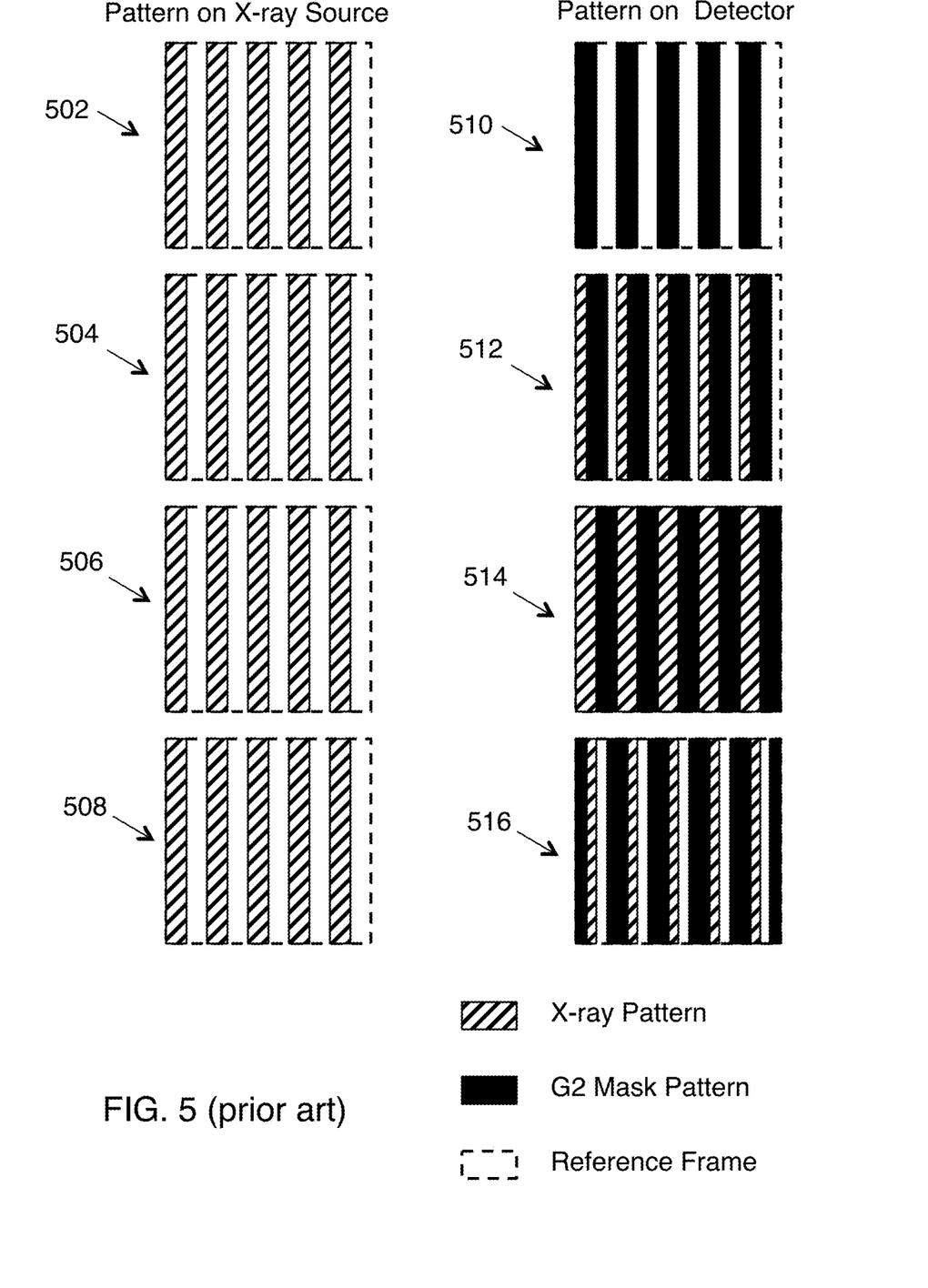
FIG. 5 shows fringe patterns in operation of the system of FIG. 1

Several methods can be used in this X-ray DPC imaging system (FIGS. 4A-B) to analyze these optical patterns. To better appreciate these methods, it is helpful to first review operation of the conventional apparatus of FIG. 1 as shown on FIG. 5. This figure shows conventional phase stepping by shifting the G2 amplitude grating with a fixed G0 amplitude grating filtered X-ray source pattern. The dotted lines show a reference frame of the X-ray source pattern and the X-ray interference pattern at the detector. Here 502, 504, 506, 508 are the same reflecting that grating G0 is fixed, while 510, 512, 514, 516 show the phase stepping at the detector. Finer phase stepping may be performed by dividing G2 amplitude grating lateral shift into finer steps. The X-ray source filtered by G0 amplitude grating is fixed. The masks of G2 amplitude grating are shown in black blocks and laterally shifted to perform phase stepping. The hatched blocks show the X-ray interference pattern formed in the scintillator of the detector. The total transmitted X-ray photons are the area integration of the X-ray interference pattern not being blocked by the masks at the detector.

There are several ways to provide this or equivalent functionality using the novel configurations of FIGS. 4A-B. These methods include: 1) shifting the PeXSA source pattern, 2) shifting or otherwise changing the mask pattern in the PcXDA detector, 3) direct detection of the fringe pattern with sufficiently small pixels in the PcXDA, and 4) use of multiple phase patterns in the PcXDA mask to provide single shot detection. These methods are described below in connection with FIGS. 6, 7, 8 and 9 respectively.

Figure 6:
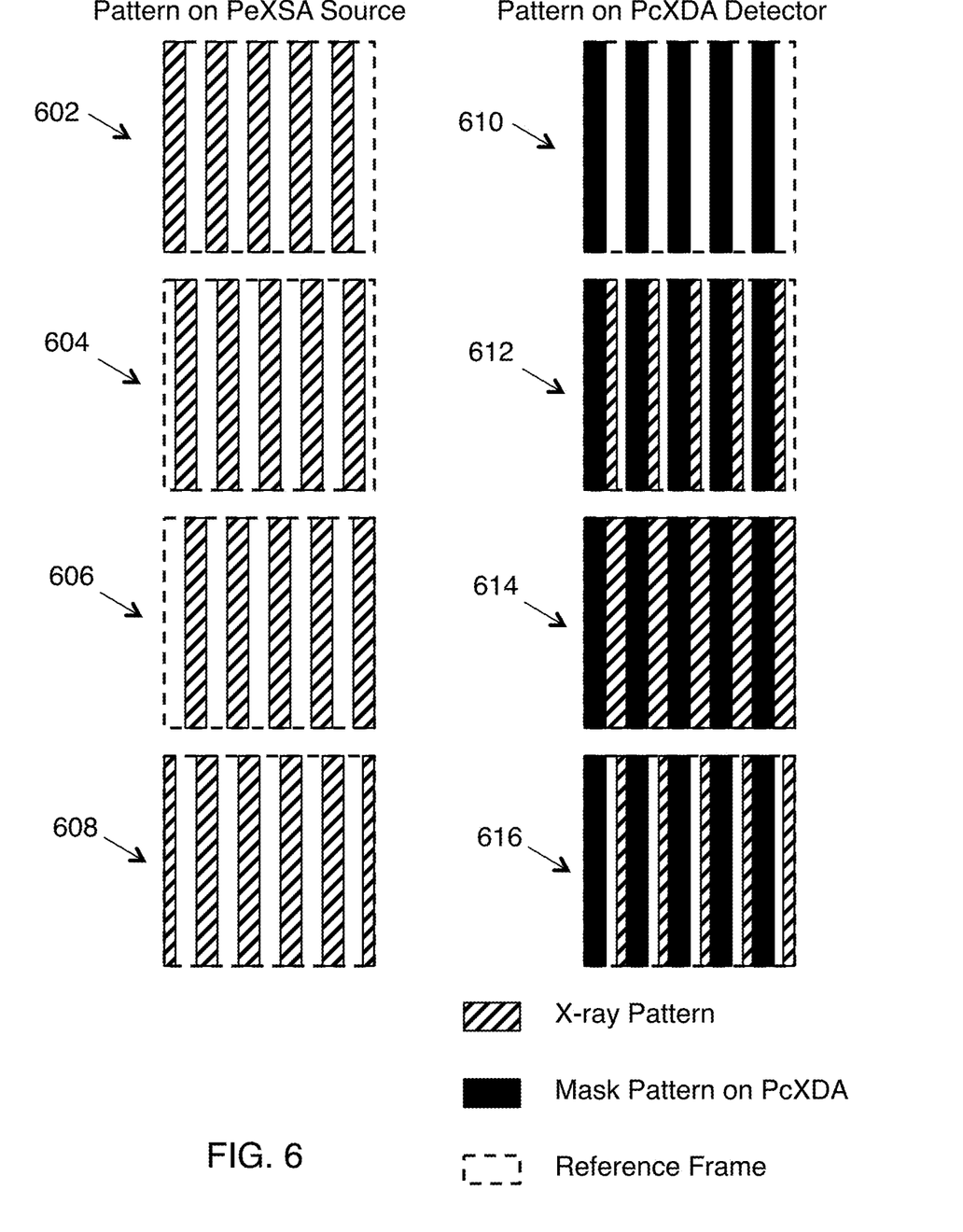
FIG. 6 shows fringe patterns in operation of the system of FIGS. 4A-B according to a first method.

FIG. 6 shows phase stepping by shifting the PeXSA X-ray source pattern. The dotted lines show a reference frame of the X-ray source pattern and the X-ray interference pattern at the detector. 602, 604, 606, 608 shows the phase stepping of the PeXSA (e.g., by changing the pattern through the spatial light modulator (SLM) or with a scanning mirror). The pattern change by the SLM is preferred because the SLM may be operated at a much faster rate (up to 32 kHz binary or more) than moving the analyzer grating G2 in FIG. 1 (~50-100 Hz per phase step). Finer phase stepping may be performed by dividing PeXSA source pattern into finer lateral shift steps. The masks in PcXDA detector are shown in black blocks and have fixed positions in this method (e.g., a fixed thin chrome light amplitude grating can be used in front of the PcXDA detector array). Here the black blocks being in the same position for 610, 612, 614, 616 show the fixed position of the PcXDA mask. The hatched blocks show the X-ray interference pattern formed in the scintillator of PcXDA detector. The total transmitted X-ray photons are the area integration of the X-ray interference pattern not being blocked by the masks at the detector.

Figure 7:
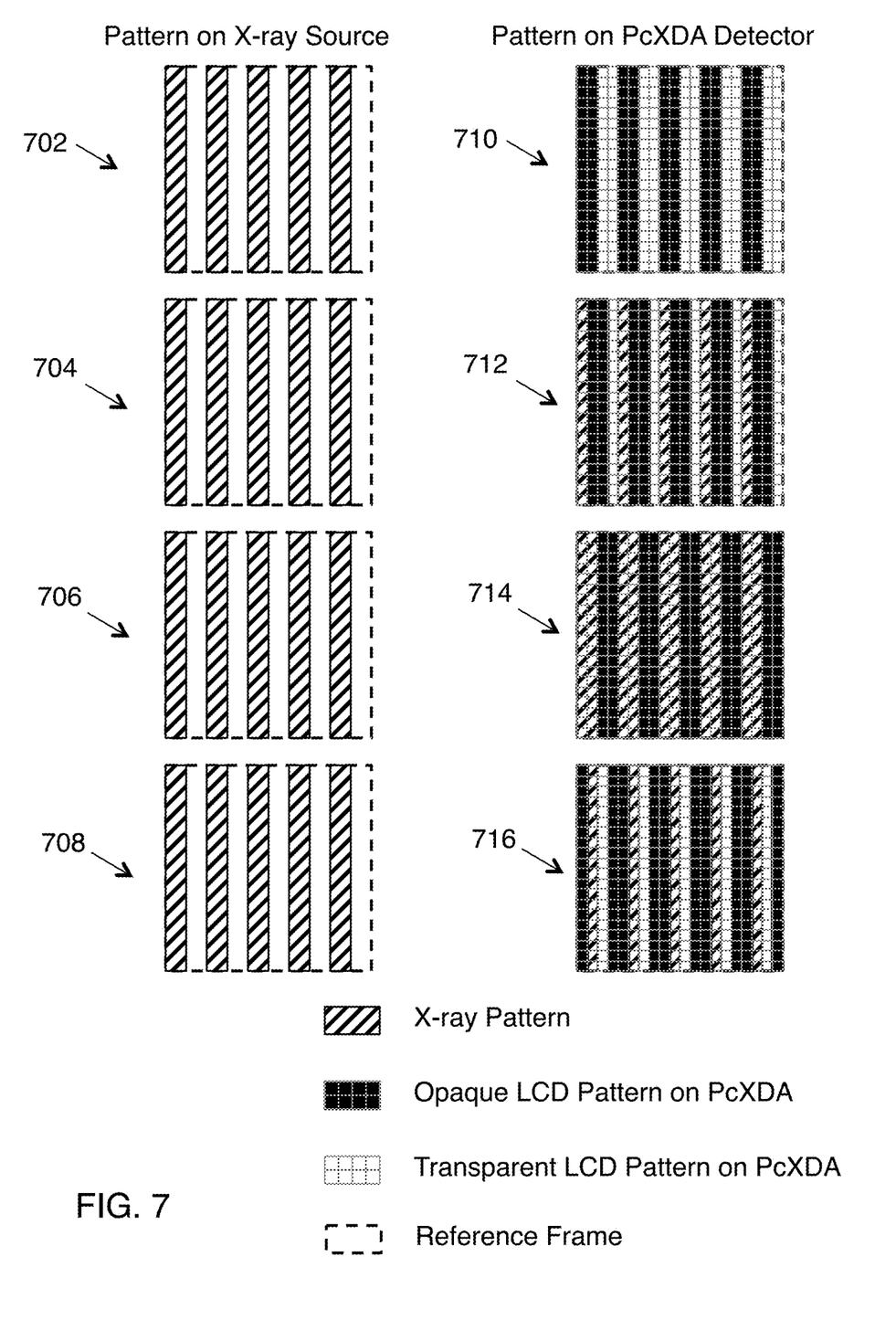
FIG. 7 shows fringe patterns in operation of the system of FIGS. 4A-B according to a second method.

FIG. 7 shows phase stepping by changing the liquid crystal mask pattern on PcXDA. The dotted lines show a reference frame of the X-ray source pattern and the X-ray interference pattern at the detector. 710, 712, 714, 716 show phase stepping by changing the PcXDA mask. Finer phase stepping may be performed by finer liquid crystal mask pixels. The PeXSA source pattern is fixed as shown by 702, 704, 706, 708. The masks of liquid crystal pattern are shown in black blocks and the pattern can be modified or scanned one column of pixels at a time. For the current commercially available technology of LCD, the smallest liquid crystal pixel size is ~<3 µm. For example, this may be used for an X-ray interference pattern with a pattern pitch of ~12 µm with four phase analyzing steps. The light hatched blocks show the X-ray interference pattern formed in the scintillator of PcXDA detector. The total transmitted X-ray photons are the area integration of the X-ray interference pattern not being blocked by the masks at the detector.

Figure 8:
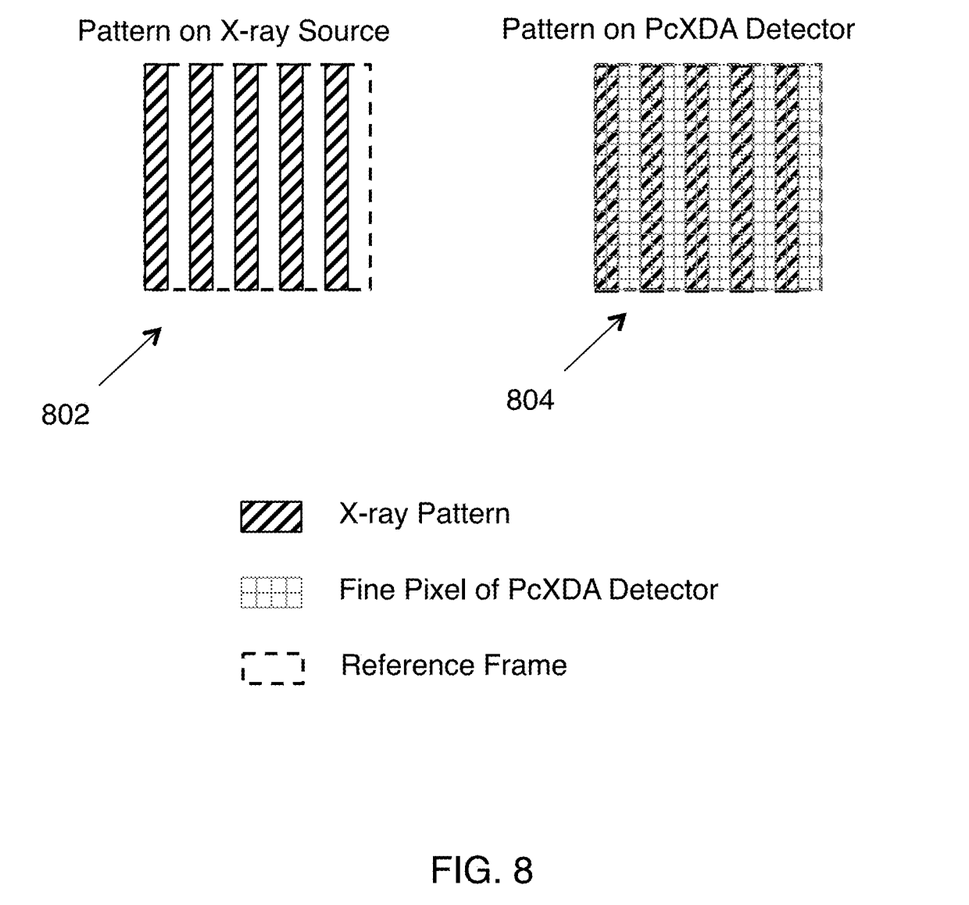
FIG. 8 shows fringe patterns in operation of the system of FIGS. 4A-B according to a third method.

FIG. 8 shows direct X-ray interference pattern detection with PcXDA and fine detector pixels. The dotted lines show a reference frame of the X-ray source pattern 802 and the X-ray interference pattern at the detector. Since the detector pixels in view 804 are fine enough to resolve the X-ray interference pattern's position, no phase stepping is needed in this DPC imaging system. The schematic design shown here has interference pattern resolution equivalent to 4-step phase stepping method. A fixed light pattern of PeXSA X-ray source is used. If the photo detector's pixel dimension is small enough (e.g., pixel size is one-forth of the X-ray interference pattern pitch with four phase analyzing steps), the chromium mask or the liquid crystal panel maybe not needed. The fine photodetector pixels are able to resolve the optical pattern transformed from the X-ray interference pattern. For the current commercially available technology, the smallest CCD detector pixel dimension is ~>1 µm. This does not work for a regular commercially available X-ray detector panel without the photonic channel implementation in PcXDA because the fluorescent light formed in the 100 µm-400 µm thick scintillator plate will blur the fluorescent image to the photodetector panel.

Figure 9:
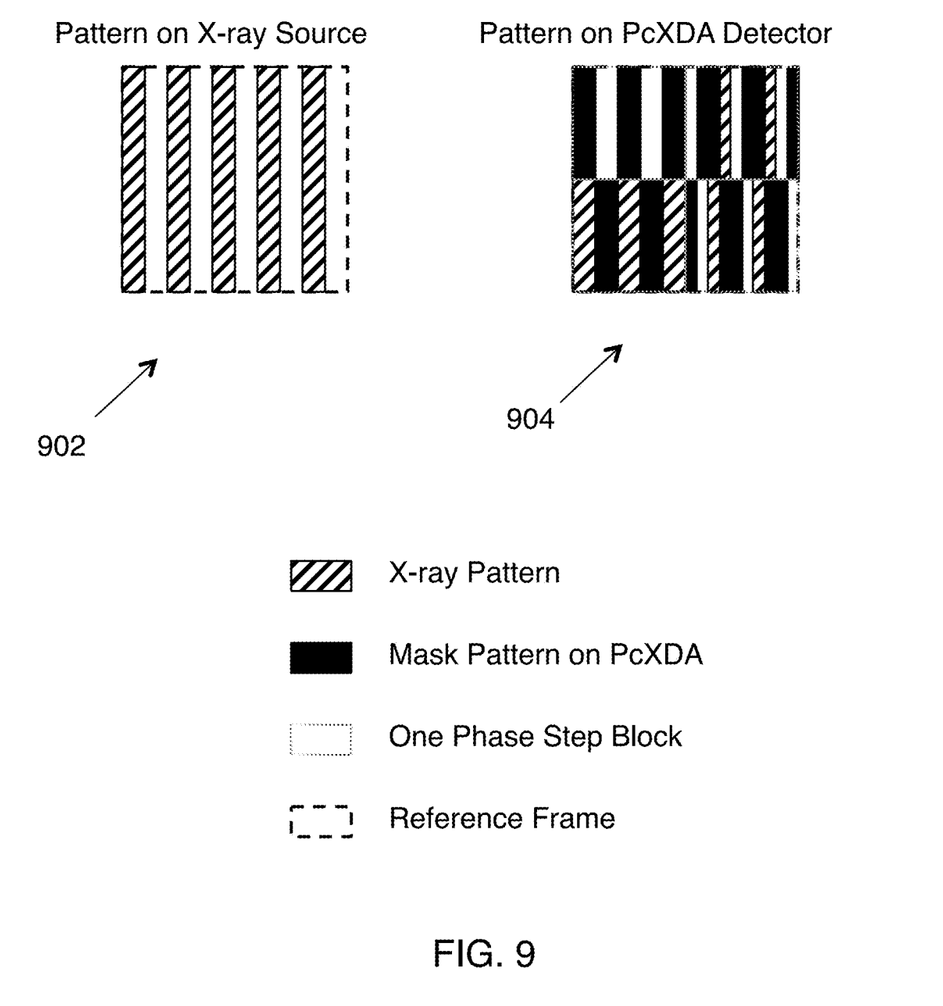
FIG. 9 shows fringe patterns in operation of the system of FIGS. 4A-B according to a fourth method.

FIG. 9 shows a single shot chromium mask grating with four phase analyzing steps. The dotted lines show a reference frame of the X-ray source pattern 902 and the X-ray interference pattern at the detector. The dotted frames in detector view 904 show each of the single phase step block (an arrangement of 4 quadrants). In each of the single phase step block, it has different phase stepping masks. From top-left, top-right, bottom-left, to bottom-right of the single phase step blocks, they have equivalent phase steps of the previously described 4-step methods. Finer phase stepping may be performed by making finer single phase step blocks. For example, if sixteen phase steps are needed, the phase step pattern can be made into 4-by-4 blocks of different single phase step mask patterns. Since both the X-ray source pattern and the mask pattern at the detector are not changed with time, the X-ray DPC signals can be obtained in "single-shot".

In another example, for N phase steps, N different phase stepping grating patterns are assigned to N detector pixels. The adjacent phase step has a lateral grating pattern shift of grating pitch/N. In the case of 4 phase steps in FIG. 9, each pixel of this 4 pixel group detects the intensity of each phase step. The information of the object is calculated according to the phase information in each of the four pixel group across the whole detector panel.

The invention claimed is:

1. Apparatus for performing X-ray differential phase contrast imaging, the apparatus comprising:
    a PeXSA X-ray source comprising a photo-emitter X-ray source array;
    a PcXDA X-ray detector comprising:
        a photonic channel X-ray detector array;
        a scintillator that converts X-ray photons to optical photons having wavelengths between 400 nm and 1000 nm, creating a corresponding optical photon light pattern;
        an optical detector array with a plurality of elements; and
        an optical system with a plurality of optical imaging systems between the scintillator and the detector array wherein the optical system images the optical photon light pattern onto an optical detector array using the plurality of optical imaging systems, wherein the PeXSA X-ray source and the PcXDA X-ray detector provide X-ray differential phase contrast imaging.

2. The apparatus of claim 1, wherein the photo-emitter X-ray source array comprises:
    a light source;
    a spatial light modulator configured to receive light from the light source and to provide an optical spatially patterned beam;
    a photocathode configured to receive the optical spatially patterned beam and to provide patterned electron emission having an electron pattern according to the optical spatially patterned beam;
    electron optics configured to receive the patterned electron emission and to provide an electron image of accelerated electrons according to the electron pattern;
    an X-ray target disposed to receive the electron image of accelerated electrons and to provide patterned X-ray emission according to the electron image.

3. The apparatus of claim 1, further comprising:
    an optical grating mask configured to mask an optical image according to a grating mask pattern.

4. Apparatus for performing X-ray differential phase contrast imaging, the apparatus comprising:
    an X-ray source comprising a photo-emitter X-ray source array;
    an X-ray detector comprising a photonic-channeled X-ray detector array, wherein the photonic-channeled X-ray detector array comprises:
        a scintillator configured to receive X-rays and to provide corresponding optical radiation;
        an optical subsystem configured to receive the optical radiation and to provide an optical image, wherein the optical subsystem comprises:
            a first telecentric lens array;

a second telecentric lens array;
a phase coded aperture disposed between the first telecentric lens array and the second telecentric lens array;
wherein the optical subsystem is configured as a 4f imaging system;
wherein a Fourier transform of the optical radiation is formed at the location of the phase coded aperture;
wherein a Fourier transform of optical radiation transmitted through the phase coded aperture is formed as the optical image at the location of the optical grating mask;
an optical detector array configured to receive the optical image and to provide a detector signal corresponding to the optical image; and
an X-ray phase grating disposed between the X-ray source and the X-ray detector;
wherein the apparatus includes no X-ray grating other than the X-ray phase grating.

5. A method of performing X-ray differential phase contrast imaging, the method comprising:
providing an apparatus for performing X-ray differential phase contrast imaging, the apparatus comprising:
a PeXSA X-ray source comprising a photo-emitter X-ray source array;
a PcXDA X-ray detector comprising:
a photonic channel X-ray detector array;
a scintillator that converts X-ray photons to optical photons having wavelengths between 400 nm and 1000 nm, an optical detector array; and
an optical system that images the optical photon light patterns onto an optical detector array using a plurality of optical imaging systems between the scintillator and the detector array and the PcXDA X-ray detector provide X-ray differential phase contrast imaging; and
analyzing X-ray fringe patterns to provide X-ray differential phase contrast imaging.

6. The method of claim 5, wherein the analyzing X-ray fringe patterns comprises scanning a detected X-ray fringe pattern by scanning an optical fringe pattern within the photo-emitter X-ray source array.

7. The method of claim 5, wherein the analyzing X-ray fringe patterns comprises scanning a detected X-ray fringe pattern by altering a transmission pattern of an optical grating mask within the photonic-channeled X-ray detector array.

8. The method of claim 7, wherein the optical grating mask comprises an array of liquid crystal optical transmission devices.

9. The method of claim 5, wherein the analyzing X-ray fringe patterns comprises analyzing a detected X-ray fringe pattern with an optical detector array, wherein the optical detector array has a pixel size of no more than 0.5 times a pitch of a detected X-ray fringe pattern.

10. The method of claim 5, wherein the analyzing X-ray fringe patterns comprises analyzing a detected X-ray fringe pattern using an optical grating mask that includes at least three distinct grating sub-mask patterns.

11. The apparatus of claim 3, wherein the optical grating mask comprises a metal of at least one of Cr, Ti, Au, Pt, Ta, Cu, and Al.

12. The apparatus of claim 3, wherein the optical grating mask has a thickness of at least 50 nm.

13. The apparatus of claim 3, wherein the optical grating mask comprises at least three distinct grating sub-mask patterns.

14. The apparatus of claim 1, further comprising an X-ray phase grating disposed between the PeXSA X-ray source and the PcXDA X-ray detector.

15. The apparatus of claim 14, wherein the apparatus includes no X-ray grating other than the X-ray phase grating.

16. The apparatus of claim 1, wherein the optical detector array is located at a conjugate imaging plane of the optical photon light pattern.

17. The method of claim 5, wherein the optical detector array is located at a conjugate imaging plane of the optical photon light pattern.

* * * * *